United States Patent [19]

Dolezal et al.

[11] 4,186,610

[45] Feb. 5, 1980

[54] APPARATUS FOR EVALUATING DEFORMATION CHARACTERISTICS OF MECHANICALLY TESTED MATERIALS

[75] Inventors: Ladislav Dolezal; Frantisek Weiss; Petr Stanek; Miroslav Lorenc, all of Brno, Czechoslovakia

[73] Assignee: Vyzkumny ustav 070, Brno, Czechoslovakia

[21] Appl. No.: 956,917

[22] Filed: Nov. 2, 1978

[51] Int. Cl.² .............................................. G01N 3/08
[52] U.S. Cl. ........................................................ 73/805
[58] Field of Search .......................... 73/805, 826, 788

[56] References Cited

U.S. PATENT DOCUMENTS

| 3,592,545 | 7/1971 | Paine et al. | 73/826 X |
| 3,885,424 | 5/1975 | Ryckman et al. | 73/805 X |

*Primary Examiner*—Jerry W. Myracle

[57] ABSTRACT

The apparatus of the invention measures and evaluates deformation characteristics of mechanically deformed test pieces, which characteristics depend upon the structural and mechanical properties of the test piece. The apparatus includes a loading device for supporting and placing a mechanical load on the test piece and a TV camera mounted for visually scanning the test piece as it is being deformed. The TV camera has an output for producing signals representative of the scanned picture. A control unit is connected to the output of the TV camera and produces control pulses responsive to the output of the TV camera and to a feedback signal from an evaluating unit. A first output of the control unit is connected to the loading device for controlling a program of mechanical load applied to the test piece. The evaluating unit has a first input connected to the output of the TV camera and second input which is connected to a second output of the control unit. The evaluating unit measures the deformation on the work piece and compares it to a deformation model producing output signals which are fed back to a second input of the control unit.

9 Claims, 2 Drawing Figures

APPARATUS FOR EVALUATING DEFORMATION CHARACTERISTICS OF MECHANICALLY TESTED MATERIALS

BACKGROUND OF THE INVENTION

The present invention relates generally to devices for testing mechanical properties of materials and more particularly to an apparatus for evaluating the deformation characteristics of test pieces placed under mechanical load.

The extent to which particular materials are deformed will logically depend upon their structural and mechanical properties. When placing cylindrical test pieces under tensile load, the test piece will become elongated and local necking-down frequently takes place. This deformation is typically evaluated at the end of the test by determining corresponding deformation coefficients.

In previously known systems for evaluating the deformation resulting from tensile load applied to test pieces, the necked-down portions of the test pieces are reviewed or studied at a point of failure when the loading forces are no longer applied. In other known devices the amount of deformation can be continuously scanned by the use of one-dimensional gauges. Motion picture cameras have also been used to record the changing shape and deformation of the test piece during the testing process. A disadvantage of the foregoing techniques and devices for evaluating deformation in test pieces is that they are limited and are incapable of taking into account all of the effects taking place in the test piece during the loading program. The known devices are particularly suited for measuring a single characteristic but cannot evaluate the total deformation characteristics of the test piece which depend upon the structural and mechanical properties of the materials. Additionally, the degree of loading in the previously known testing devices cannot be controlled (by varying the loading program) in response to shape changes or deformation taking place in the test piece. It has been found to be an advantage to be able to control the loading program of a testing device so that such loading could correspond to predetermined alternatives for the progressive structural deformation of the material being tested as well as in response to any damage of the test piece. This ability could provide significant information in analyzing the materials being tested.

It is accordingly a principal object of the present invention to provide an apparatus for measuring and evaluating deformation characteristics of mechanically deformed test pieces which overcomes the disadvantages of the known devices.

A more specific object of the present invention is to provide an apparatus of the foregoing type which includes means for visually scanning the deformation taking place in a test piece under mechanical load and evaluating such deformation based on predefined models.

A further object of the present invention is to provide an apparatus for evaluating the deformation characteristics of mechanically deformed materials which has means connected to the loading device for controlling the loading program depending upon the deformation characteristics perceived.

Other objects, features and advantages of the present invention will become more apparent from the description of the invention in connection with the accompanying drawings which will be described more fully hereinafter.

SUMMARY OF THE INVENTION

The foregoing objects are generally accomplished by providing an apparatus for measuring and evaluating the deformation characteristics of a mechanically deformed test piece which has means for controlling the loading program of the test piece in accordance with a predefined structural-mechanical plastic-deformation model. The apparatus includes a loading device for supporting and placing a mechanical load on a test piece to deform the test piece and a TV camera mounted for visually scanning the test piece as it is being deformed. A control unit is connected to the output of the TV camera for transforming picture signals into control pulses. A first output of the control unit is connected to the loading device for controlling the loading program applied to the test piece. An evaluating unit is also connected to the output of the TV camera and has means for measuring the deformation of the work piece and comparing the deformation to a predefined structural-mechanical plastic-deformation model and for producing output signals responsive to the deformation. A second output of the control unit is connected to a second input of the evaluating unit and a feedback path connects the output of the evaluating unit to an input of the control unit so that the control pulses produced by the control unit are proportional to the signals produced by the evaluating unit.

By means of the input from the control unit, the evaluating unit transforms the picture signals produced by the scan of the test piece by the TV camera into quantitative signs, such as analytical functions forming the geometric figures observed. The output of the evaluating unit can be used to control the speed of scanning and to control the loading device in response to the deformation characteristics, such as moments of symmetrical contour, coefficients of expansion, differential forms, etc. so that optimized testing procedures depending upon the reaction of the material and conditions of the loading can be achieved.

The device of the present invention is particularly suited for laboratory research into material properties and for use in quality control procedures to check material properties which are required to have specific deformation characteristics.

In one embodiment of the present invention, the picture of the test piece being deformed and as scanned by a TV camera can be produced by suitable illumination, or alternatively in complicated situations, can be produced by using laser holography techniques. The video signal produced by the output of the camera contains pulses in each line scanned which contrast with the background. The pulses are supplied to the evaluating unit and are synchronized by the line and picture frequency of the camera. The pulses are then processed in the evaluating unit by an appropriate logic system. The result is stored in a memory of the evaluating unit. A computer within the evaluating unit completes the function of the evaluating unit and produces an output which can be fed back to the control unit for controlling the loading program. The computer also serves to check and control synchronization of the pulses.

BRIEF DESCRIPTION OF THE DRAWINGS

The foregoing and other features of the apparatus according to the present invention will be more fully described with reference to the following drawings annexed hereto, in which.

DESCRIPTION OF THE INVENTION

Figure 1:
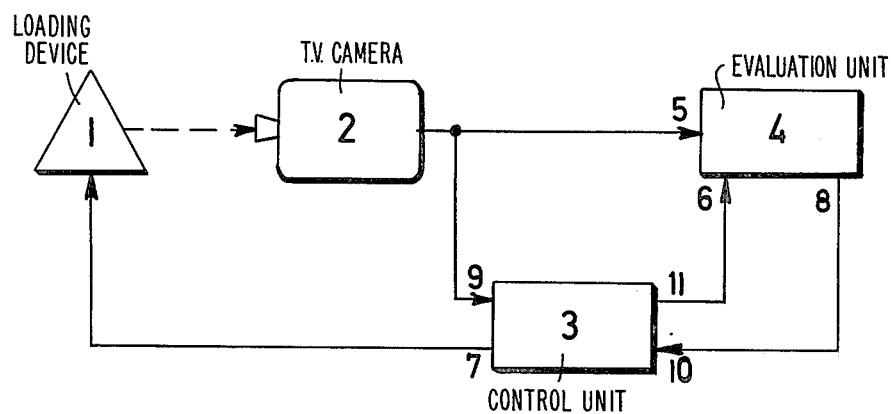
FIG. 1 is a block diagram illustrating the principal components of the invention and their interconnection.

Referring now in more detail to the accompanying drawings, FIG. 1 generally illustrates the present invention in which a loading device 1 is used for supporting and applying a mechanical load to a test piece to produce mechanical deformation. A TV camera 2 is mounted for visually scanning the test piece in the loading device 1. The TV camera produces an output signal which is connected to a first input 9 of a control unit 3. The control unit 3 produces a synchronizing pulse at an output 11. The control unit also produces pulses at output 7 which is connected to the loading device 1 for controlling the loading program. An evaluating unit 4 for evaluating the deformation characteristics scanned by the TV camera has its input 5 connected to the output of the TV camera. The output 8 of the evaluating unit is connected by a feedback path to a second input 10 of the control unit 3 so that control of the loading machine depends upon the signals produced by the evaluating unit.

Figure 2:
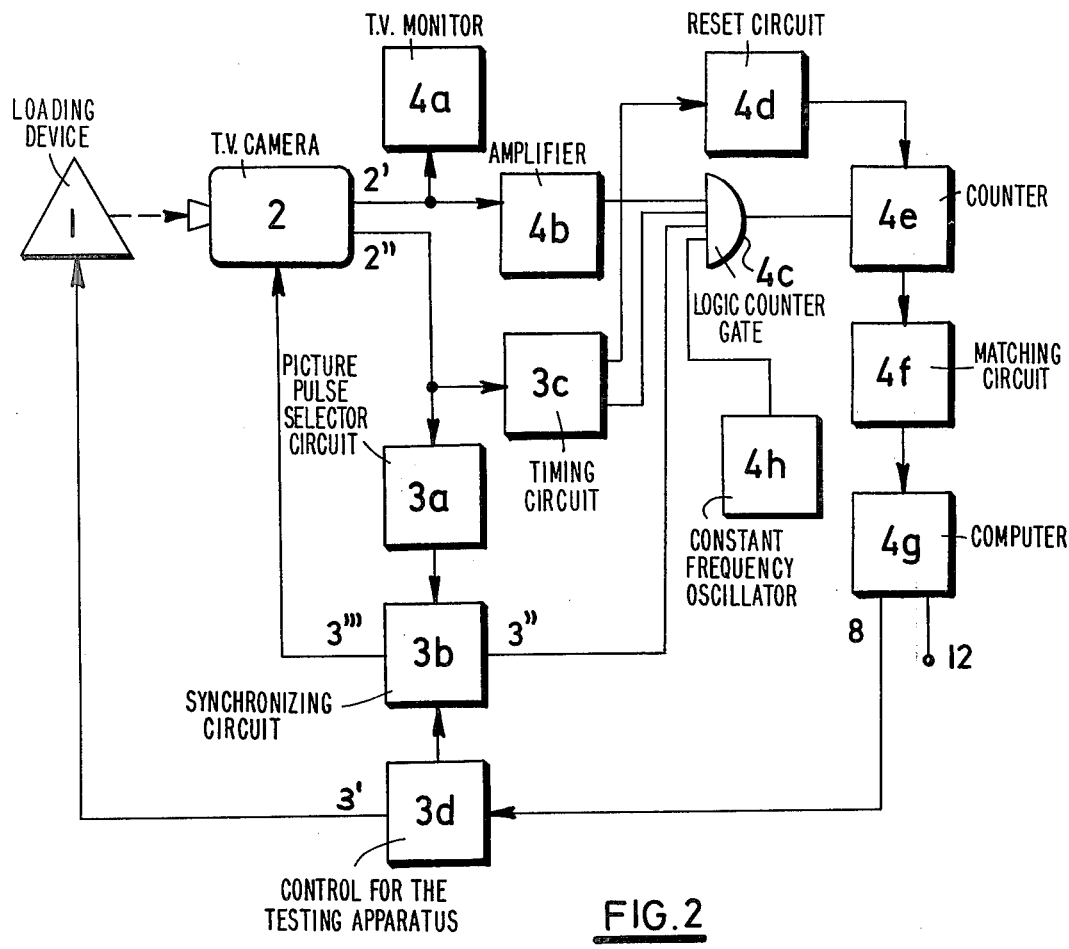
FIG. 2 is a block diagram of a particular embodiment of the present invention illustrating particular functions within each of the main components.

Referring now to FIG. 2, the details of the control unit and evaluating unit are shown in block diagramatic form. As seen in this figure, camera 2 produces a video signal at output 2' and a synchronizing signal at output 2". A TV monitor 4a is connected to output 2' so that the scanned image can be viewed for correcting the position and focusing of the camera and for monitoring the progress of the deformation on the test piece. The output 2' is also connected to an input of a video signal amplifier 4b forming part of the evaluating unit 4.

Output 2" is connected to the input of a timing circuit 3c which determines the time period in which the video signal is evaluated, and removes synchronizing pulses which may be contained in the video signal. Timing circuit 3c comprises two monostable sweep circuits, the first of which is started by a horizontal synchronizing pulse. The output 2" of the TV camera is also connected to a picture pulse selector circuit 3a. This circuit is an integrator and has an output which produces picture-synchronizing pulses. The output of the picture pulse selector 3a carries picture synchronization pulses which are connected to a circuit 3b and are used for synchronizing the apparatus of the invention. A starting pulse 3' is fed to another input of circuit 3b. By the starting pulse 3' an R-S sweep circuit is triggered in the circuit 3b, which by its output unlocks another sweep circuit connected as divider by two, on the input of which is connected the output of the picture pulse selector circuit 3a. After unlocking of the divider by two, the next picture pulse, causes a signal 3" to be produced on its output, which is then cleared by the following picture pulse 3". By resetting the divider by two into its initial position, the R-S sweep circuit is inversely cleared, whereby the divider by two is relocked. Consequently, the signal 3" is lasting just for an interval of one picture and after it has been cleared, the circuit 3b is prepared to receive the next starting pulse 3'. In this manner the particular moment for evaluating deformation characteristics can be selected.

The output of signal amplifier 4b is connected to a logic product gate 4c. Signal 3" from the output of circuit 3b, which defines the duration of a single picture is also connected to the gate 4c. A constant freqency oscillator 4h also provides a signal which is connected to the gate 4c. The signal from the output of the timing circuit 3c is also coupled with the gate 4c and the combined signal from the output of gate 4c is connected to a counter 4e.

The numbers of pulses having a frequency corresponding to the frequency of the oscillator 4h, which are counted by the counter 4e in each line scanned by the TV camera and fed via the video signal amplifier to the gate 4c, is proportional to the width of the test piece at that point in the scan for the line counted. The information from the counter 4e is then fed to a matching circuit 4f and then to the input of computer 4g where the counted values are stored. The matching circuit 4f is a standard interface for connecting a peripheral input device to the computer. The counter 4e is then reset by a pulse from a reset circuit 4d which is controlled by the timing circuit 3c. The computer 4g evaluates the deformation characteristics of materials tested on the basis of the geometric shape of the loaded test pieces and the data concerning the force and elongation in time, these being either empirical values or physical parameters established by a proper evaluation program. As desired by the experimenter, the course of loading as well as the frequency of scanning can be programmed. The computer 4g has an output 12 which can be used for schematically representing the deformation characteristics of the test piece. On the basis of the deformation characteristics evaluated, the computer 4g produces on its output 8 both an order for scanning another picture and the data for controlling the testing apparatus by means of the circuit 3d. From the order for scanning another picture a starting pulse 3' is derived in the circuit 3d by means of a monostable sweep circuit. Moreover, the circuit 3d comprises digital-to-analog converters converting the digital information from the output 8 of the computer 4g into the analog form for controlling the power members of the loading device 1, thus controlling the course of loading.

The rectilinear speed of scanning by the camera 2 can also be controlled as is schematically represented by the output signal 3'" of the control circuit 3b. For this purpose an astable multivibrator having a frequency corresponding to the speed of storing the input data into the memory of the computer 4g is provided in the circuit 3b.

The apparatus of the present invention is useful for obtaining information about the behavior of materials when placed under various loading conditions which can be simulated by simple tensile tests. This apparatus is particularly useful with respect to evaluating material and deformation characteristics where predefined conditions of material strength represented by particular deformation characteristics can be tested by applying controlled loads in a particular program.

Additional quantitative parameters of deformation in the test piece can be evaluated by the apparatus of the invention by placing a variety of markings on the test piece. Alternatively, other deformation characteristics such as the degree of linear extension, can be simultaneously fed to the input of the evaluating unit for simultaneous evaluation.

While the present invention has been described and illustrated with respect to a particular embodiment, which produces satisfactory results, it will be appreciated by those skilled in the art, after understanding the purposes of the invention, that various other changes and modifications may be made without departing from the spirit and scope of the invention, and it is therefore intended to cover all such changes and modifications in the appended claims.

What is claimed is:

1. An apparatus for measuring and evaluating deformation characteristics of mechanically deformed test pieces comprising, a loading device for supporting and continuously placing a mechanical load on a test piece to deform said test piece, a TV camera mounted for visually scanning said test piece as it is being deformed, said TV camera having an output producing electrical signals representative of a scanned picture of said test piece, a control unit connected to the output of said TV camera for transforming picture signals into control pulses, a first output of said control unit being connected to said loading device for controlling mechanical load applied to said test piece, an evaluating unit having a first input thereof connected to the output of said TV camera and a second input thereof connected to a second output of said control unit, said evaluating unit having means for measuring deformation characteristics of said work piece and for producing an output signal at a first output thereof, and a feedback path connecting said first output of said evaluating unit with a second input of said control unit, whereby said control unit produces control pulses for controlling load applied to said test piece.

2. The apparatus according to claim 1 further comprising means connected to the output of said TV camera for visually determining position and focusing characteristics of said camera.

3. The apparatus according to claim 2 wherein said position and focusing means is a TV receiver-monitor.

4. The apparatus according to claim 1 wherein said control unit comprises a picture pulse selector circuit connected to an output of said TV camera for receiving synchronizing signals therefrom and producing picture synchronizing pulses, a circuit connected to the output of said picture pulse selector circuit for producing an output signal fed to the evaluating unit, and a timing circuit connected to the output of said TV camera for producing a timing signal connected to said evaluating unit.

5. The apparatus according to claim 4 further comprising means connecting said control unit with said TV camera for controlling the speed of scan of said camera.

6. The apparatus according to claim 1 wherein said evaluating unit comprises a video signal amplifier having an input connected to the output of said TV camera for receiving a video signal therefrom, a product gate connected to the output of said video signal amplifier, said gate connected to the output of said timing circuit of said control unit, a constant frequency oscillator connected to the input of said gate, a counter having an input connected to the output of said gate, a matching circuit having an input connected to the output of said counter, and a computer having an input connected to the output of said matching circuit.

7. The apparatus according to claim 6 wherein said computer has an output connected to an input of said control unit for producing a starting pulse of said control unit for initiating an evaluating step of a picture line scan.

8. The apparatus according to claim 6 wherein said computer has additional output means for schematically representing the deformation characteristics evaluated by said evaluating unit.

9. The apparatus according to claim 6 further comprising a reset circuit having an input connected to the output of said timing circuit and an output thereof connected to the counter for resetting said counter.

* * * * *

UNITED STATES PATENT AND TRADEMARK OFFICE
CERTIFICATE OF CORRECTION

PATENT NO. : 4,186,610

DATED : February 5, 1980

INVENTOR(S) : Petr Stanek, Miroslav Lorenc, Ladislav Dolezal, Frantisek Weiss.

It is certified that error appears in the above-identified patent and that said Letters Patent are hereby corrected as shown below:

Change the order of the inventors, appearing on the front page of the above-identified patent from "Ladislav Dolezal; Frantisek Weiss; Petr Stanek; Miroslav Lorenc, "

to
-- Petr Stanek; Miroslav Lorenc; Ladislav Dolezal; Frantisek Weiss, --

Signed and Sealed this

Eleventh Day of November 1980

[SEAL]

Attest:

SIDNEY A. DIAMOND

Attesting Officer

Commissioner of Patents and Trademark